(12) United States Patent
Richer

(10) Patent No.: US 12,369,983 B2
(45) Date of Patent: *Jul. 29, 2025

(54) SYSTEMS AND METHODS FOR IDENTIFYING ABLATION LOCATIONS USING PRINCIPAL COMPONENT ANALYSIS

(71) Applicant: St. Jude Medical, Cardiology Division, Inc., St. Paul, MN (US)

(72) Inventor: Louis-Philippe Richer, Montreal (CA)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 103 days.

This patent is subject to a terminal disclaimer.

(21) Appl. No.: 18/316,430

(22) Filed: May 12, 2023

(65) Prior Publication Data

US 2023/0277248 A1    Sep. 7, 2023

Related U.S. Application Data

(63) Continuation of application No. 17/034,400, filed on Sep. 28, 2020, now Pat. No. 11,684,424.

(Continued)

(51) Int. Cl.
*A61B 34/10*  (2016.01)
*A61B 18/12*  (2006.01)
(Continued)

(52) U.S. Cl.
CPC ............. *A61B 34/10* (2016.02); *A61B 18/12* (2013.01); *G16H 30/40* (2018.01);
(Continued)

(58) Field of Classification Search
CPC .............. A61B 34/10; A61B 18/12; A61B 2018/00577; A61B 2034/107;
(Continued)

(56) References Cited

U.S. PATENT DOCUMENTS

2019/0090749 A1   3/2019   Leuthardt et al.
2019/0365265 A1   12/2019  Grouchy et al.

OTHER PUBLICATIONS

Yamashita et al. "Image Integration to Guide Catheter Ablation in Scar-Related Ventricular Tachycardia", Journal of Cardiovascular Electrophysiology, vol. 27, No. 6, Jun. 2016, 699-708.

(Continued)

*Primary Examiner* — Ashley K Buran
*Assistant Examiner* — Zainab Mohammed Aldarraji
(74) *Attorney, Agent, or Firm* — Armstrong Teasdale LLP

(57) ABSTRACT

Systems and methods for identifying potential ablation sites using principal component analysis (PCA) are provided. A method includes generating a dataset for analysis, the dataset including a plurality of variables and generated using imaging data associated with a three-dimensional geometry that includes a plurality of vertices. The method further includes performing PCA on the generated dataset to identify a plurality of principal components and to generate, for each vertex of the plurality of vertices, a score associated with each of the plurality of principal components. The method further includes transposing the scores for each vertex onto the three-dimensional geometry, and displaying, using the computing device, the three-dimensional geometry including the transposed scores to facilitate identifying potential ablation sites.

20 Claims, 19 Drawing Sheets

Related U.S. Application Data

(60) Provisional application No. 62/909,305, filed on Oct. 2, 2019.

(51) Int. Cl.
 *G16H 30/40* (2018.01)
 *A61B 18/00* (2006.01)
 *A61B 90/00* (2016.01)

(52) U.S. Cl.
 CPC ............ *A61B 2018/00577* (2013.01); *A61B 2034/107* (2016.02); *A61B 2090/367* (2016.02)

(58) Field of Classification Search
 CPC ........ A61B 2090/367; A61B 2034/105; A61B 2018/00904; G16H 30/40; G16H 20/40
 See application file for complete search history.

(56) References Cited

OTHER PUBLICATIONS

Piers et al. "Imaging-guided Ventricular Tachycardia Ablation", Arrhythm Electrophysiol Rev. Nov. 2013;2(2):128-34.

Yamashita et al. "Impact of New Technologies and Approaches for Post-Myocardial Infarction Ventricular Tachycardia Ablation During Long-Term Follow-Up", Circ Arrhythm Electrophysiol. Jul. 2016;9(7). pii: e003901.

Kumar S, Baldinger SH, Romero J, Fujii A, Mahida SN, Tedrow UB, Stevenson WG, "Substrate-Based Ablation Versus Ablation Guided by Activation and Entrainment Mapping for Ventricular Tachycardia: A Systematic Review and Meta-Analysis.", J Cardiovasc Electrophysiol. Dec. 2016;27(12):1437-1447.

Greisas et al., "Detection of Abnormal Cardiac Activity Using Principal Component Analysis—A Theoretical Study", IEEE Transactions on Biomedical Engineering, vol. 62, No. 1, Jan. 2015, doi: 10.1109/TBME.2014.2342792, Epub. Jul. 25, 2014., PMID: 25073163, pp. 154-164.

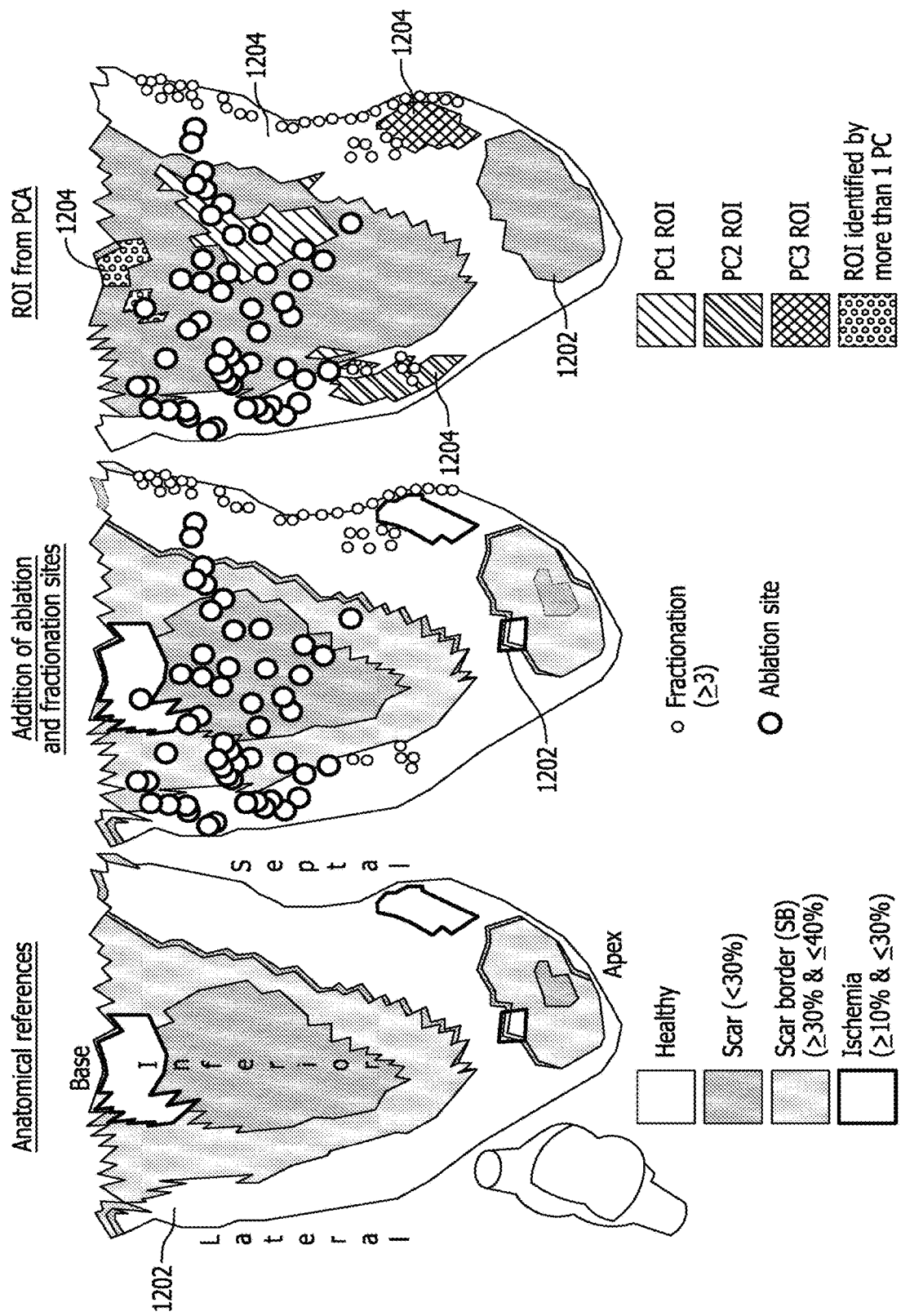

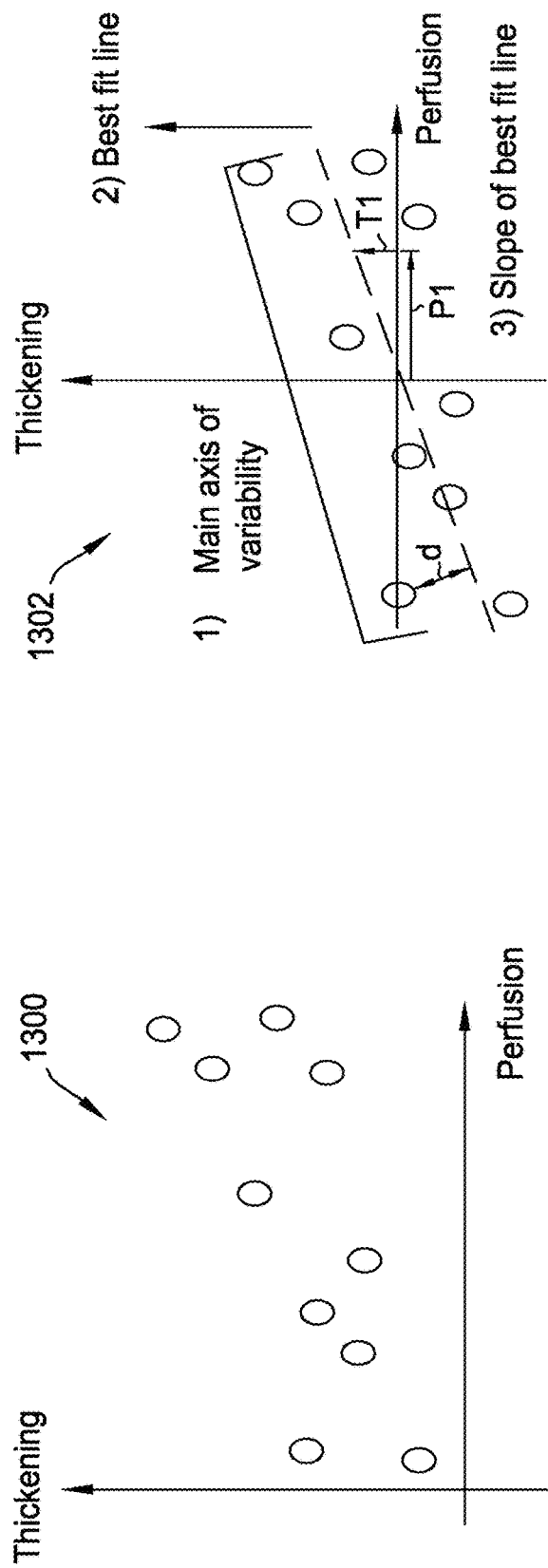
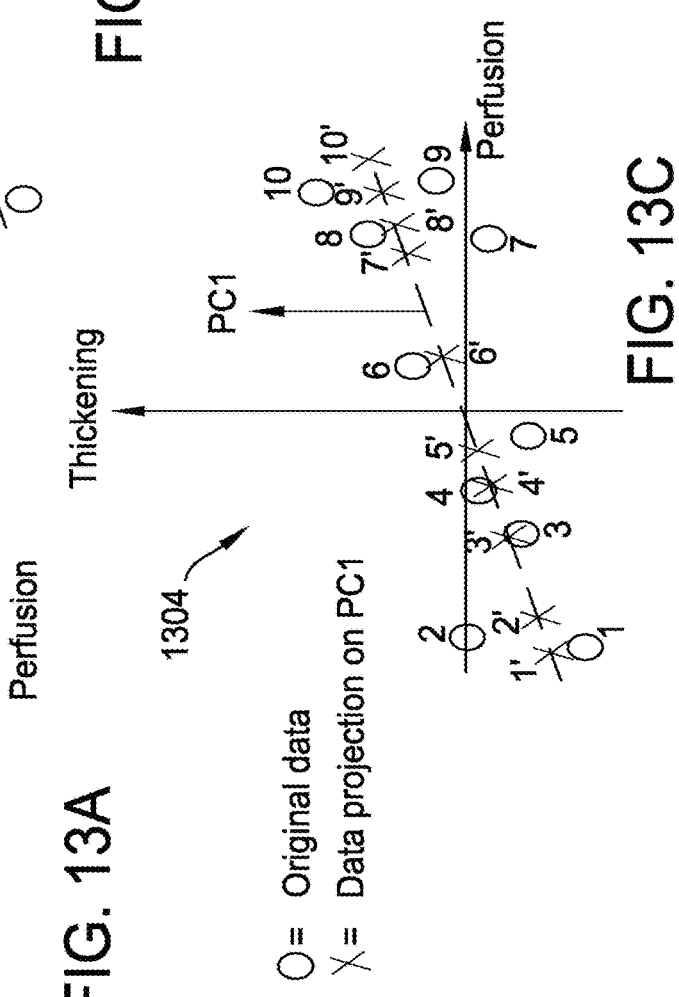
FIG. 13A
FIG. 13B
FIG. 13C

O = Original data
× = Data projection on PC1
△ = Data projection on PC2

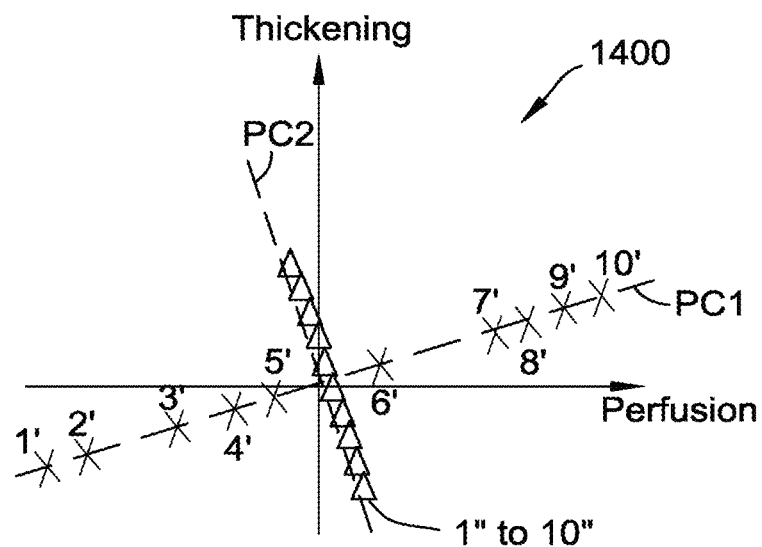
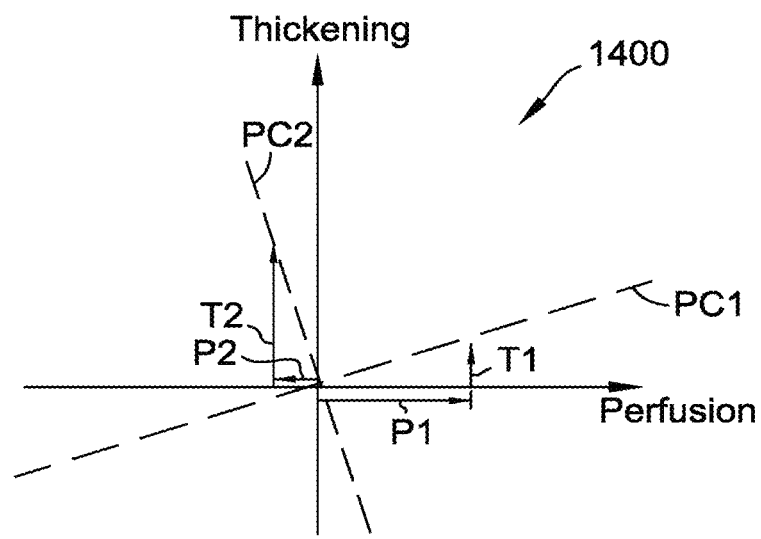
FIG. 14A

⟋ 1404

PC1                PC1 WEIGH
         SCORES/CHANNEL           VECTOR

10   X                   0
             9   X                   0
                       IF X IN SIGNIF
             8   X     ZONE THEN      0
                       CORRESP                    REPEAT FOR
             7   X                   0     ──────▶    PC2
        #
        x    6   X     ─────────▶    0
        e
        t    5   X     CHANNEL IN    0
        r
        e                WEIGHT
        V    4   X       VECTOR      0
                        SET TO 1
             3   X                   1
             2   X                   1
             1   X                   1

SYSTEMS AND METHODS FOR IDENTIFYING ABLATION LOCATIONS USING PRINCIPAL COMPONENT ANALYSIS

CROSS REFERENCE TO RELATED APPLICATIONS

This application is a continuation of U.S. application Ser. No. 17/034,400, filed Sep. 28, 2020, which claims priority to provisional application Ser. No. 62/909,305, filed Oct. 2, 2019, both of which are incorporated herein by reference in their entirety.

FIELD OF THE DISCLOSURE

The present disclosure relates generally to tissue ablation systems. In particular, the present disclosure relates to identifying potential ablation locations using principal component analysis.

BACKGROUND

Radiofrequency (RF) ablation is often an effective treatment strategy for patients with ventricular tachycardia (VT). To improve efficacy of RF ablation, it is generally desirable to identify locations that, when ablated, will likely reduce VT. When VT is not inducible or not hemodynamically tolerated, a clinician may attempt to identify a VT substrate for ablation during a stable sinus or paced rhythm. Substrate-based approaches generally involve identification of low voltage areas consistent with scar and abnormal electrograms that represent surviving myocytes capable of supporting re-entrant VT circuits. Such approaches may be heavily dependent on using extensive electro-anatomical mapping (EAM) to delineate low voltage areas, and to identify abnormal electrograms (i.e., fragmented electrograms and late potentials).

However, there are certain limitations to EAM. For example, EAM is relatively time-consuming, and may result in inaccurate delineation of intramural scars in some situations. Accordingly, given the availability of different imaging modalities (that may provide detailed anatomical information characterizing myocardial scars), as well as progress in image acquisition and processing, at least some clinical electrophysiologists have integrated imaging data into VT ablation procedures. Three-dimensional image integration does help improve clinical outcomes for VT ablation, but may also increase dataset complexity. For example, the time taken by a clinician to determine whether all relevant information has been extracted/sorted from imaging data, and to interpret the resulting maps may be as time-consuming as EAM itself.

Moreover, bridging imaging data with voltage data and ensuring that all aspects of the data are considered before starting an ablation procedure may be challenging. This may result in clinicians relying on voltage data alone without considering imaging data when making clinical decisions, eliminating any benefits realized by using imaging data. Accordingly, it would be desirable to incorporate imaging data with a simplified dataset that classifies the relevance of the data to the arrhythmic substrate.

BRIEF SUMMARY OF THE DISCLOSURE

In one embodiment, the present disclosure is directed to a computer-implemented method for identifying potential ablation sites using principal component analysis (PCA). The method includes generating, using a computing device, a dataset for analysis, the dataset including a plurality of variables and generated using imaging data associated with a three-dimensional geometry that includes a plurality of vertices, performing, using the computing device, PCA on the generated dataset to identify a plurality of principal components and to generate, for each vertex of the plurality of vertices, a score associated with each of the plurality of principal components, transposing, using the computing device, the scores for each vertex onto the three-dimensional geometry, and displaying, using the computing device, the three-dimensional geometry including the transposed scores to facilitate identifying potential ablation sites.

In another embodiment, the present disclosure is directed to a computing device for identifying potential ablation sites using principal component analysis (PCA). The computing device includes a memory device and a processor communicatively coupled to the memory device. The processor is configured to generate a dataset for analysis, the dataset including a plurality of variables and generated using imaging data associated with a three-dimensional geometry that includes a plurality of vertices, perform PCA on the generated dataset to identify a plurality of principal components and to generate, for each vertex of the plurality of vertices, a score associated with each of the plurality of principal components, transpose the scores for each vertex onto the three-dimensional geometry, and display the three-dimensional geometry including the transposed scores to facilitate identifying potential ablation sites.

In yet another embodiment, the present disclosure is directed to non-transitory computer-readable media having computer-executable instructions thereon. When executed by a processor of a computing device, the instructions cause the processor of the computing device to generate a dataset for analysis, the dataset including a plurality of variables and generated using imaging data associated with a three-dimensional geometry that includes a plurality of vertices, perform PCA on the generated dataset to identify a plurality of principal components and to generate, for each vertex of the plurality of vertices, a score associated with each of the plurality of principal components, transpose the scores for each vertex onto the three-dimensional geometry, and display the three-dimensional geometry including the transposed scores to facilitate identifying potential ablation sites.

The foregoing and other aspects, features, details, utilities and advantages of the present disclosure will be apparent from reading the following description and claims, and from reviewing the accompanying drawings.

BRIEF DESCRIPTION OF THE DRAWINGS

FIGS. 12A-12C illustrate a comparison between at least some known ablation determination techniques and the systems and methods described herein.

FIGS. 13A-13E illustrate steps for an example PCA analysis.

FIGS. 14A-14E illustrate steps for an example of PCA data processing performed to compute an arrhythmogenic index using the data shown in FIGS. 13A-13E.

DETAILED DESCRIPTION OF THE DISCLOSURE

The present disclosure provides systems and methods for identifying potential ablation sites using principal component analysis (PCA). A method includes generating a dataset for analysis, the dataset including a plurality of variables and generated using imaging data associated with a three-dimensional geometry that includes a plurality of vertices. The method further includes performing PCA on the generated dataset to identify a plurality of principal components and to generate, for each vertex of the plurality of vertices, a score associated with each of the plurality of principal components. The method further includes transposing the scores for each vertex onto the three-dimensional geometry, and displaying the three-dimensional geometry including the transposed scores to facilitate identifying potential ablation sites.

The systems and method described herein use a combination of imaging data, descriptive statistics of local regions around vertices in the imaging data, and principal component analysis (PCA) to perform a pre-procedural exploratory data analysis and identify potential ablation locations. These embodiments simplify datasets, easing comprehension by clinicians and enabling the clinicians to easily extract substantially all useful information from the datasets.

As will be appreciated by those of skill in the art, PCA is a mathematical tool capable of identifying patterns in complex datasets, and to determine which variables influence a particular parameter the most. In the embodiments described herein, statistics are computed over a surface of fixed radius around each vertex of a three-dimensional geometry to identify regions of high perfusion variability. Subsequently, mapping data is normalized and processed using PCA to determine principal components that have the greatest influence on high perfusion variability, as described herein. When enough principal components (e.g., three components) are identified such that a certain percentage (e.g., 80%) of the dataset variance is explainable, then those components are used to determine regions of interest to consider for ablation. Specifically, scores for the principal components are plotted on the three-dimensional geometry, and a color scale of the displayed geometry is adjusted to specific intervals, as described herein. Accordingly, the systems and methods described herein leverage PCA to perform a pre-procedural identification of regions of interest to be considered for ablation by a clinician.

Figure 1:
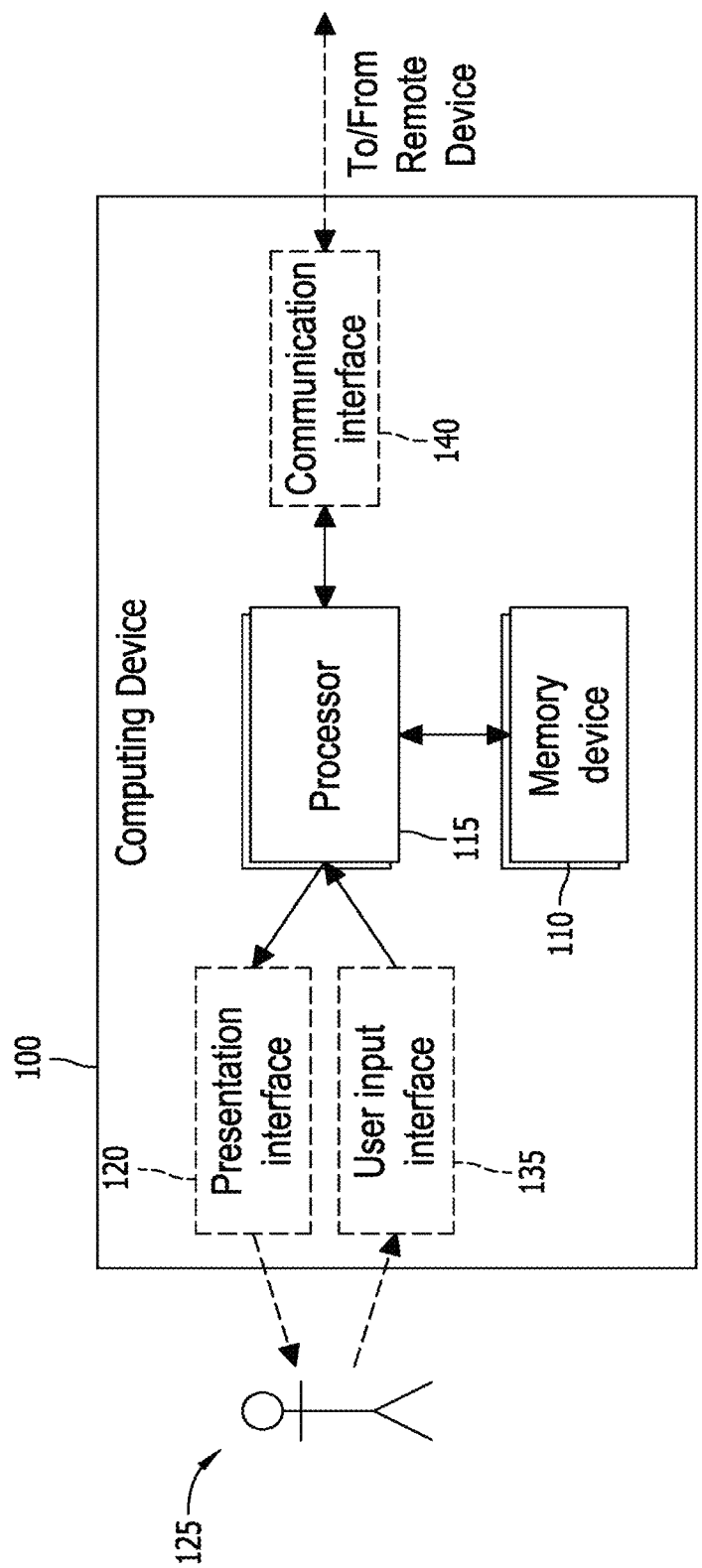
FIG. 1 is a block diagram of one embodiment of a computing device that may be used to implement the systems and methods described herein.

Referring now to the drawings wherein like reference numerals are used to identify identical components in the various views, FIG. 1 illustrates one embodiment of a computing device 100 that may be used to implement the systems and methods described herein. Computing device 100 includes at least one memory device 110 and a processor 115 that is coupled to memory device 110 for executing instructions. In some embodiments, executable instructions are stored in memory device 110. In this embodiment, computing device 100 performs one or more operations described herein by programming processor 115. For example, processor 115 may be programmed by encoding an operation as one or more executable instructions and by providing the executable instructions in memory device 110.

Processor 115 may include one or more processing units (e.g., in a multi-core configuration). Further, processor 115 may be implemented using one or more heterogeneous processor systems in which a main processor is present with secondary processors on a single chip. In another illustrative example, processor 115 may be a symmetric multi-processor system containing multiple processors of the same type. Further, processor 115 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In this embodiment, memory device 110 is one or more devices that enable information such as executable instructions and/or other data to be stored and retrieved. Memory device 110 may include one or more computer readable media, such as, without limitation, dynamic random access memory (DRAM), static random access memory (SRAM), a solid state disk, and/or a hard disk. Memory device 110 may be configured to store, without limitation, application source code, application object code, source code portions of interest, object code portions of interest, configuration data, execution events and/or any other type of data.

In this embodiment, computing device 100 includes a presentation interface 120 that is coupled to processor 115. Presentation interface 120 presents information to a user 125. For example, presentation interface 120 may include a display adapter (not shown) that may be coupled to a display device, such as a cathode ray tube (CRT), a liquid crystal display (LCD), an organic LED (OLED) display, and/or an "electronic ink" display. In some embodiments, presentation interface 120 includes one or more display devices. Input signals and/or filtered signals processed using the embodiments described herein may be displayed on presentation interface 120.

In this embodiment, computing device 100 includes a user input interface 135. User input interface 135 is coupled to processor 115 and receives input from user 125. User input interface 135 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 120 and user input interface 135.

Computing device 100, in this embodiment, includes a communication interface 140 coupled to processor 115. Communication interface 140 communicates with one or more remote devices. To communicate with remote devices, communication interface 140 may include, for example, a wired network adapter, a wireless network adapter, and/or a mobile telecommunications adapter.

As described in detail herein, computing device 100 executes an algorithm to identify potential ablation regions for a clinician. Specifically, computing device 100 generates a dataset for analysis using a three-dimensional geometry, analyzes the dataset using PCA to identify a predetermined number of principal components, and projects scores for at least one of the predetermined number of principal components onto the three-dimensional geometry to identify potential ablation locations, as described herein.

Figure 2:
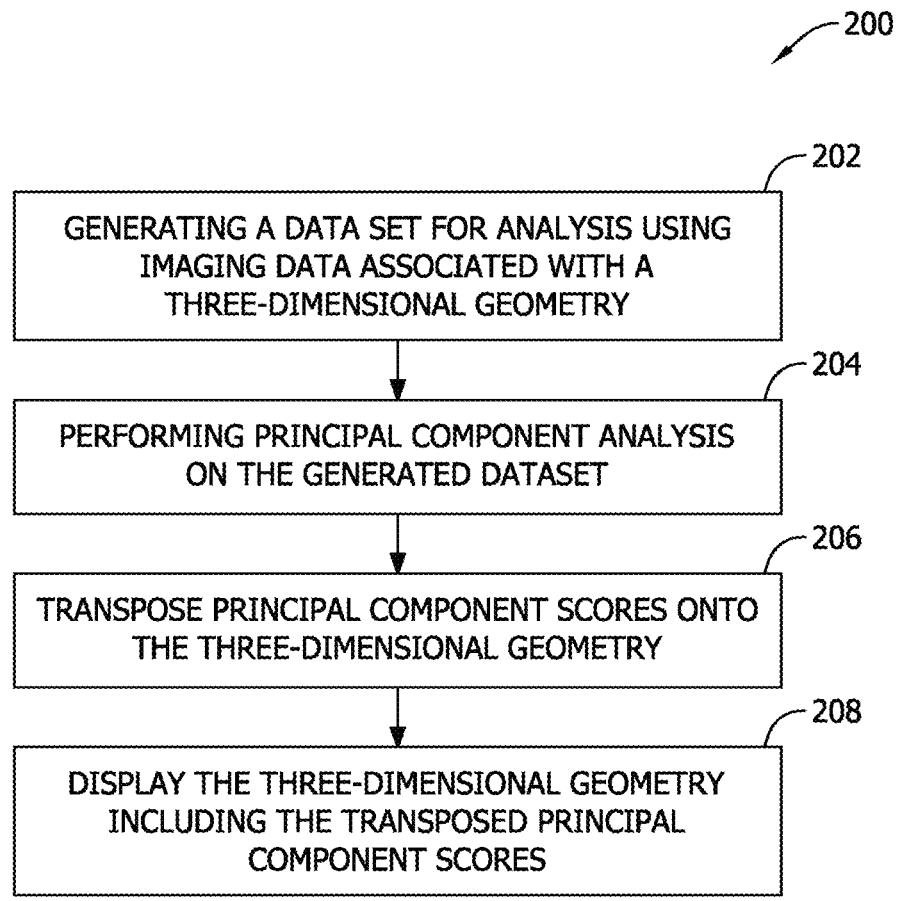
FIG. 2 is a block diagram of a method of identifying potential ablation locations using principal component analysis (PCA).

FIG. 2 is a block diagram of a method 200 of identifying potential ablation locations using PCA. Method 200 may be implemented, for example, by computing device 100 (shown in FIG. 1).

Method 200 includes generating 202 a dataset for analysis. The dataset may be generated, for example, using imaging data associated with a three-dimensional geometry including a plurality of vertices. The imaging data may include electrophysiological (EP) mapping data, magnetic resonance imaging (MRI) data, computed tomography (CT) data, ultrasound imaging data, etc. In one embodiment, the dataset includes a combination of raw variables (e.g., perfusion values at rest), as well as processed variables.

The processed variables may be generated by computing descriptive statistics for each vertex in the three-dimensional geometry. In one embodiment, the descriptive statistics are computed for each vertex based on all neighboring vertices within a predetermined radius of the particular vertex. The predetermined radius may be, for example, 0.5 centimeters (cm). Alternatively, any suitable predetermined radius may be used to compute the descriptive statistics.

Figure 3:
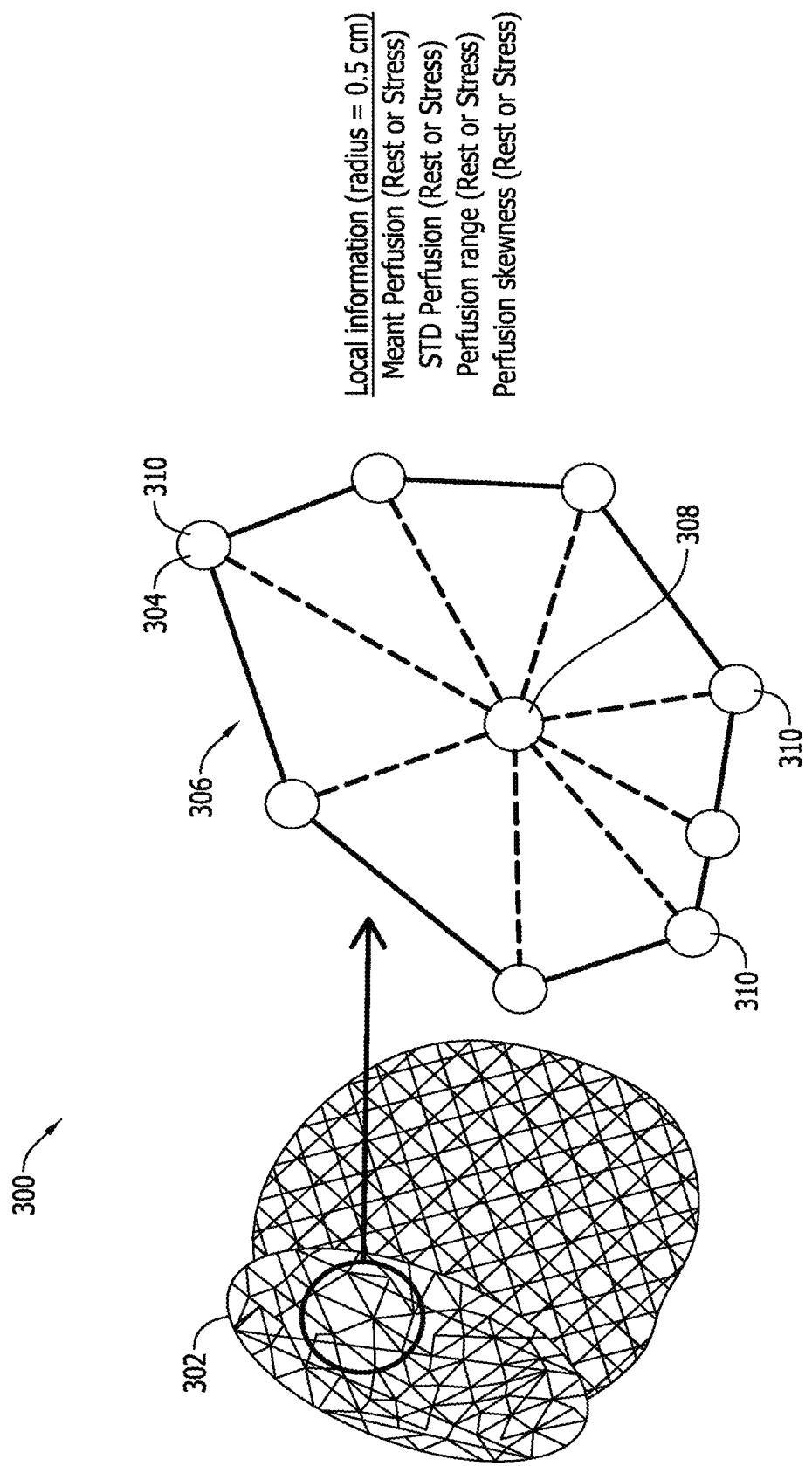
FIG. 3 is a diagram illustrating calculation of local descriptive statistics.

FIG. 3 is a diagram 300 illustrating calculation of local descriptive statistics. Specifically, diagram 300 shows a geometric mesh 302 generated using single-photon emission computed tomography (SPECT). Those of skill in the art will appreciate that geometric mesh may alternatively be generated using any other suitable imaging modality. Geometric mesh 302 is an example of a three-dimensional geometry. Geometric mesh 302 includes a plurality of vertices 304, each vertex 304 having associated physiological information (e.g., perfusion, fibrosis, and/or innervation values). An enlarged portion 306 of geometric mesh 302 is also shown in FIG. 3. Enlarged portion 306 includes a vertex of interest 308 (for which local descriptive statistics for the physiological information are calculated), and a plurality of neighboring vertices 310. Neighboring vertices 310 are vertices located within a predetermined radius (here, 0.5 cm) of vertex of interest 308. In this embodiment, the statistics calculated (i.e., the processed variables) include mean perfusion, standard deviation of perfusion, perfusion range, and perfusion skewness. Perfusion skewness indicates symmetry/asymmetry information about the distribution of values in the neighborhood of vertex of interest 308 (e.g., are the majority of values greater than a mean of the distribution, less than the mean of the distribution, or relatively evenly distributed about the mean). Each of these statistics may be calculated at rest and/or stress.

These statistics are relevant to determining potential ablation locations, as they can unveil regions of high variability that may be involved in initiation and/or maintenance of arrhythmia. Further, when perfusion data following stress (e.g., pharmacological stress) is available, differences between various perfusion parameters at different physiological states (i.e., rest and stress) can be computed as well. The more aspects associated with the ventricular substrate included in the dataset (e.g., different physiological states, raw variables, local descriptive statistics), the better the characterization of the ventricular substrate for PCA analysis and, ultimately, the better the identification of potential ablation locations. However, to avoid skewing results, the same information should not be included in the dataset twice. For example, it would be undesirable to include in the dataset multiple variables regarding data dispersion in the local descriptive statistics.

Referring back to FIG. 2, once the dataset is generated 202, method 200 further includes performing 204 PCA on the dataset. Notably, PCA is performed 204 on the dataset pre-procedurally, so that potential ablation locations are identified in advance. Prior to performing 204 PCA, in some embodiments, the data in the dataset is scaled, or normalized, to improve the PCA and eliminate discrepancies. That is, if the dataset includes different data with difference scaling, PCA will always be skewed toward the data with the greatest variability. For example, if the dataset includes variables for perfusion (which includes data ranging from 0% to 100%) and standard deviation of perfusion (which includes data ranging from 0% and 15%), without scaling or normalization, PCA will always classify the variable with the greatest range (here, perfusion), as the greatest source of variability. Thus, to ensure that all variables are expressed over the same range, a feature normalization scaling process may be applied such that all data falls within a range of [0, 1]. If all variables already have the same scale in the dataset (e.g., if the variables include perfusion data before and after inducing stress), normalization is not required.

Performing 204 PCA identifies a number of principal components that explain variance in the dataset in ascending order. That is, the first principal component explains the most variation in the dataset, the second component explains the second most variation in the dataset, etc. Performing 204 PCA also generates, for each identified principal component, a score for each vertex in the three-dimensional geometry. Further, for each identified principal component, a loading for each variable in the dataset is calculated. The loading for a particular variable relative to a particular principal component indicates how influential that variable is on the score for that principal component.

Figure 4:
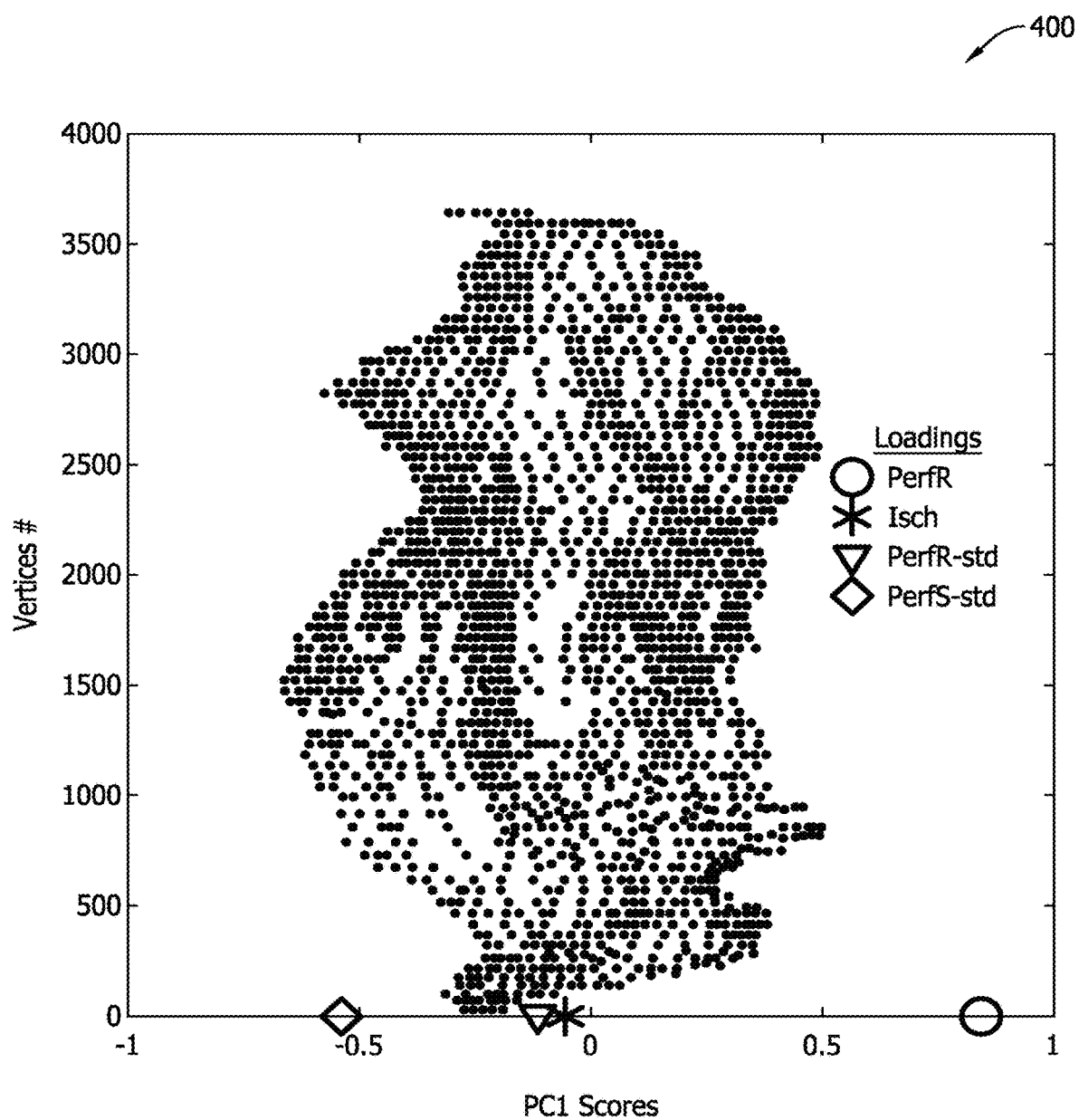
FIG. 4 is a graph illustrating scores for a first principal component for each vertex of a three-dimensional geometry.

For Example, FIG. 4 is a graph 400 illustrating scores for a first principal component. The scores shown in graph 400 were generated by applying PCA to a dataset including the following variables: perfusion at rest (PerfR), ischemia (Isch), standard deviation of perfusion at rest (PerfR-std), and standard deviation of perfusion under stress (PerfS-std). Those of skill in the art will appreciate that these four variables are merely exemplary, and that any suitable variables may be included in the dataset on which PCA is performed 204.

As shown in graph 400, for the first principal component, the scores for each vertex (represented as dots on graph 400) fall between −1 and +1. The loading for each variable in the dataset is shown on the x-axis of graph 400. Notably, the loading for Isch and PerfR-std indicates that these two variables have relatively little influence on the first principal component score (i.e., the loading for Isch and PerfR-std is relatively close to zero). In contrast, PerfR and PerfS-std are more influential on the score, and are located further from zero on the x-axis.

Referring back to FIG. 2, to identify potential ablation locations, the principal component scores are transposed 206 onto the three-dimensional geometry, and the three-dimensional geometry including the transposed principal component scores is displayed 208 (e.g., to a clinician).

Figure 5:
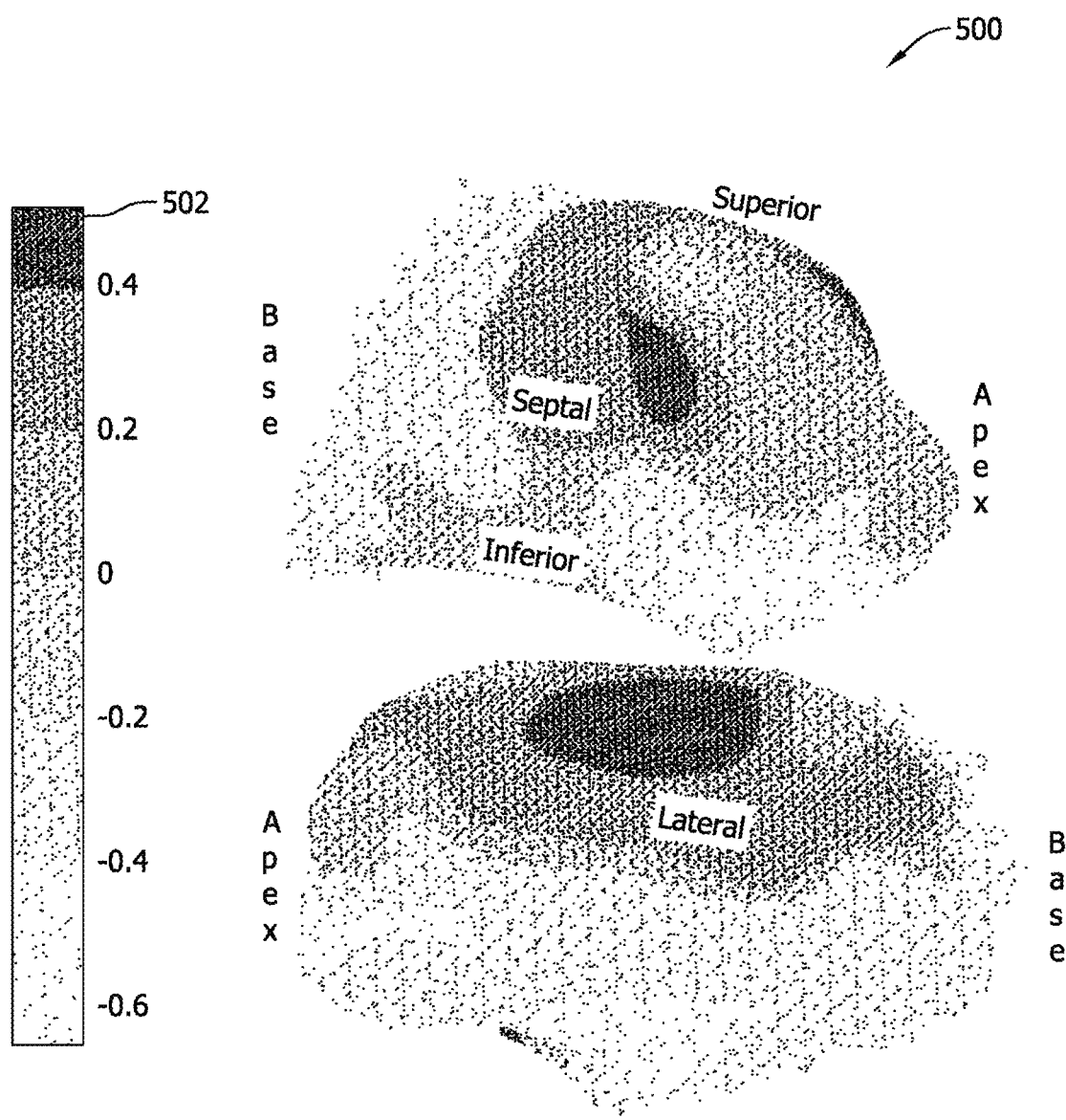
FIG. 5 is a diagram in which the scores from FIG. 4 have been transposed onto the three-dimensional geometry.

For example, FIG. 5 is a diagram 500 in which the scores from graph 400 have been transposed onto a three-dimensional geometry (here, the left ventricle (LV)). A color scale 502 in FIG. 5 enables visualization of variation across all scores from graph 400. However, scores that correspond to the loading of variables furthest away from zero are more likely to identify better ablation locations. That is, scores around loadings represent vertices for which the loadings have the highest influence. Further, in graph 400, vertices with the lowest perfusion (which generally corresponds to LV scar (which is a desirable ablation location). Accordingly, vertices with scores opposite of the loading for PerfR are of interest in graph 400.

Figure 6:
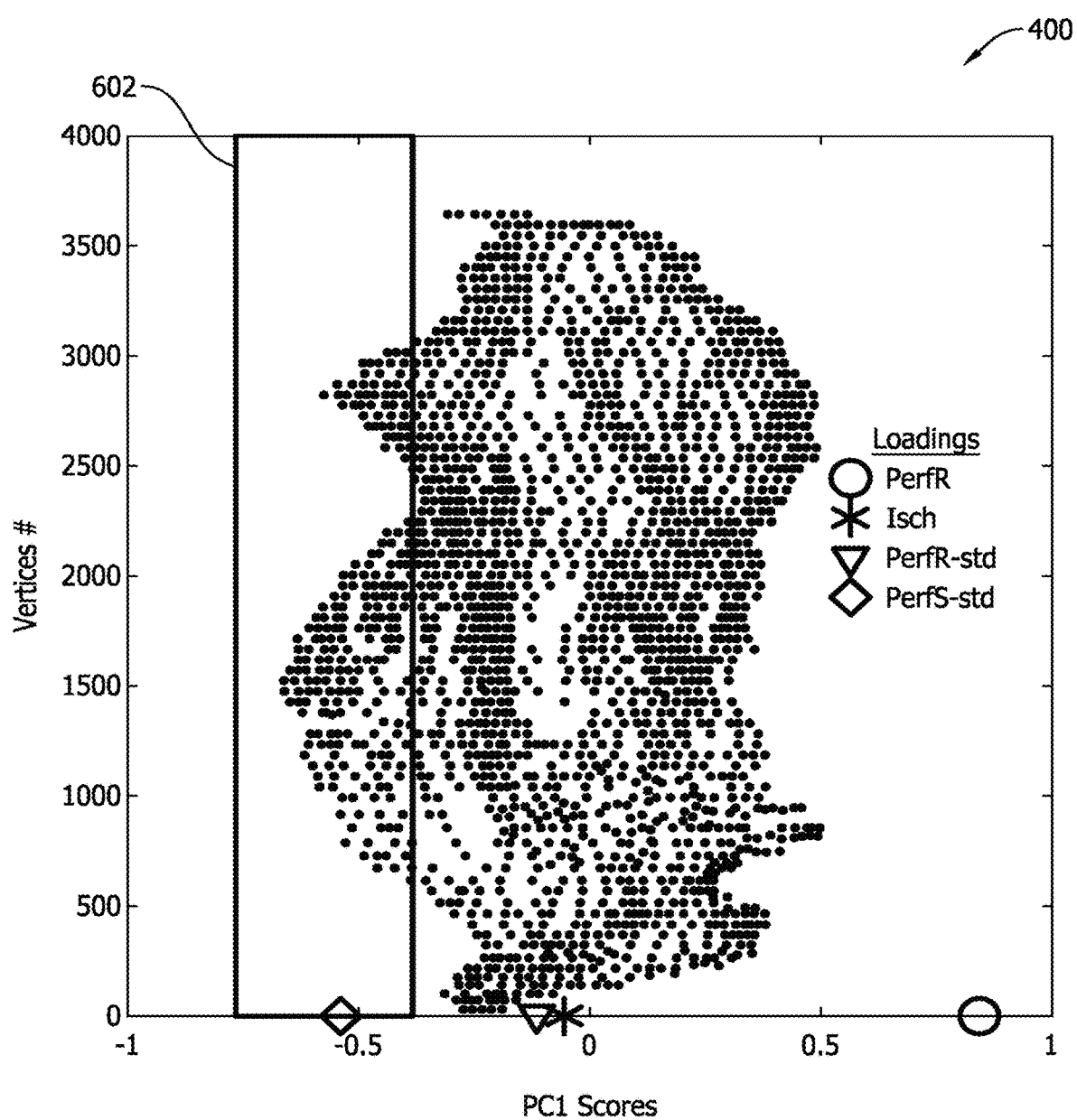
FIG. 6 is graph illustrating scores for the first principal component with a score window overlaid and indicating scores of interest.

Accordingly, FIG. 6 shows graph 400 with a score window 602 overlaid. Score window 602 is aligned with the loading for PerfS-std, and contains a subset of all of the vertexes (specifically, vertexes with scores that are approximately equal to the loading for PerfS-std). Score window 602 may be automatically generated by a computing device (e.g., computing device 100 (shown in FIG. 1)), or may be defined and generated by a user operating a user interface on a computing device. For example, the user (or computing device) may select score window 602 to include data on the extremes of graph 400 (e.g., above 0.5 or below −0.5).

Figure 7:
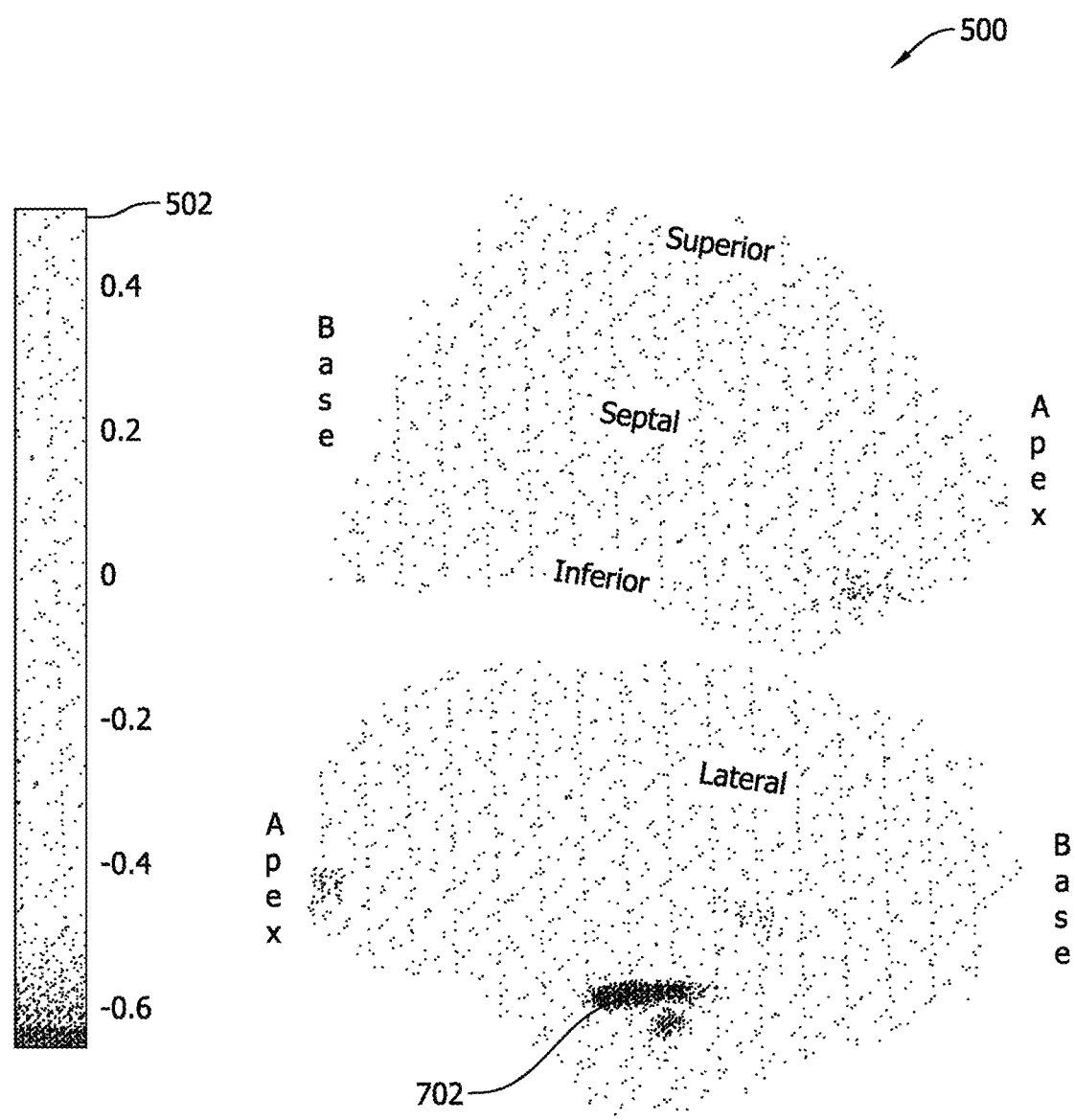
FIG. 7 is a diagram in which the scores from FIG. 6 have been transposed onto the three-dimensional geometry.

FIG. 7 shows diagram 500 with the color scale 502 adjusted to emphasize scores within score window 602. As shown in FIG. 7, this adjustment highlights a region of interest 702 of the three-dimensional geometry, clearly identifying a potential ablation site.

This process is repeated for the other principal components in order until at least a predetermined percentage (e.g., 80%) of the variance in the dataset is explained. For example, because each principal component explains a certain percentage of the total variance, the percentages explained by each principal component may be summed (starting with the first principal component) until the sum is greater than or equal to 80%. For example, calculating scores for the first three principal components may result in explaining more than 80% of the variance. Those of skill in the art will appreciate that 80% is an example threshold, and that higher or lower thresholds may be set in alternative embodiments. The percentage of variance explained by each principal component may be computer by i) summing squared distances between each score for that principal component and the origin, ii) dividing the summation by the number of scores for that principal component minus one (which gives the data variability explained per principal component), and iii) dividing the data variability per principal component by the total data variability to obtain a percentage of data variability explained by the associated principal component.

Figure 8:
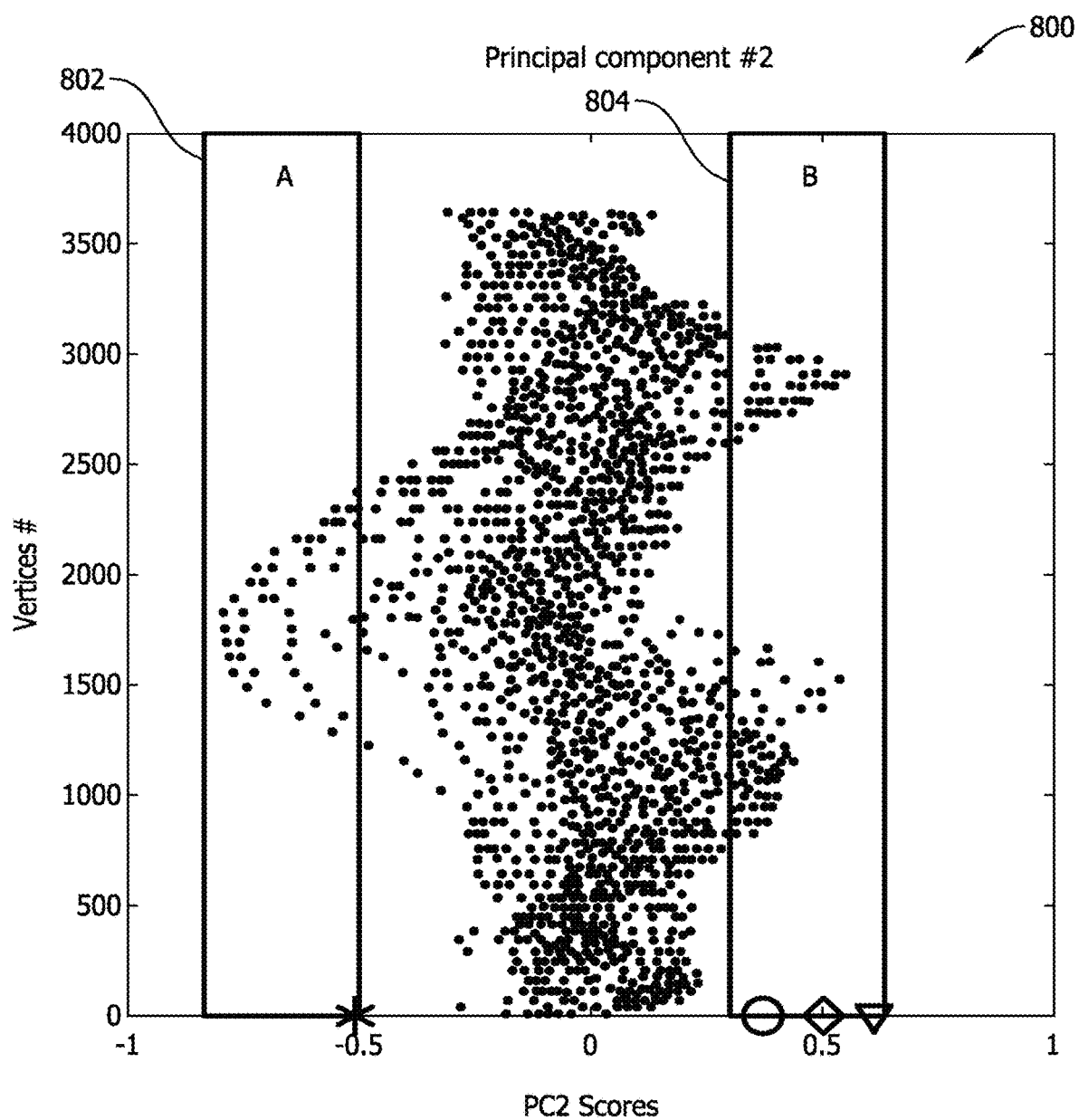
FIG. 8 is a graph illustrating scores for a second principal component.
Figure 9:
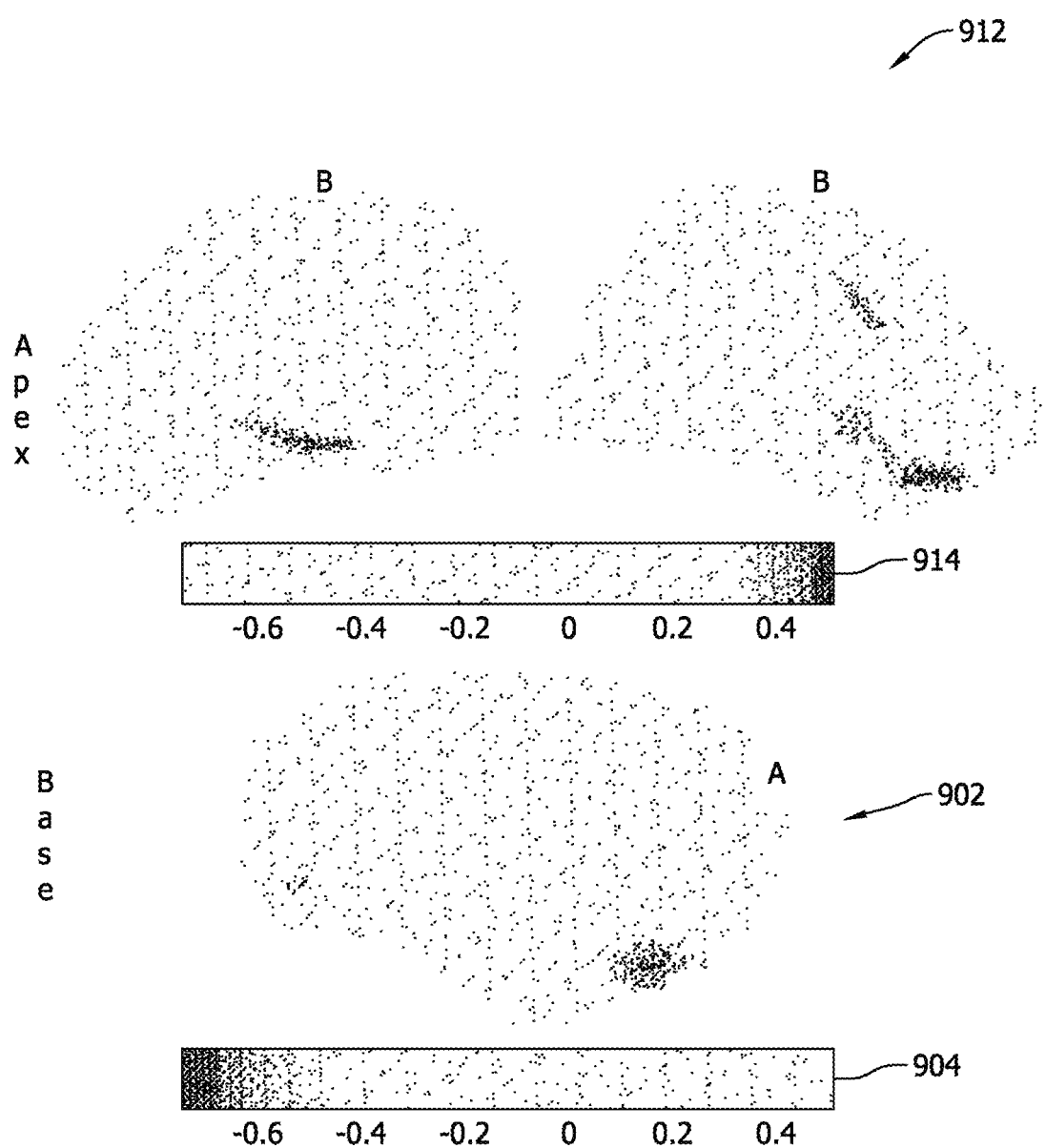
FIG. 9 is a diagram in which the scores from FIG. 8 have been transposed onto a three-dimensional geometry.
Figure 10:
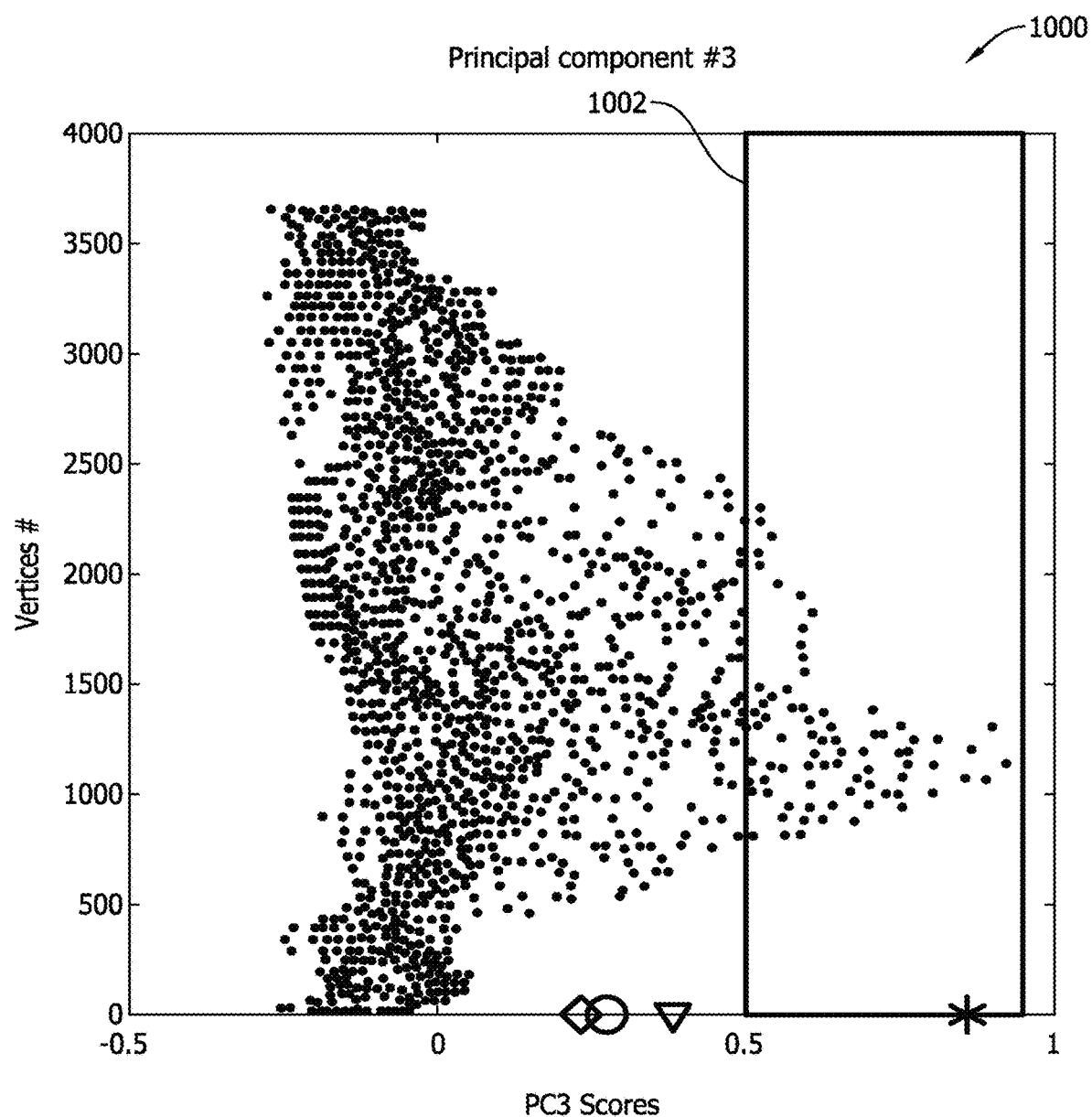
FIG. 10 is a graph illustrating scores for a third principal component.
Figure 11:
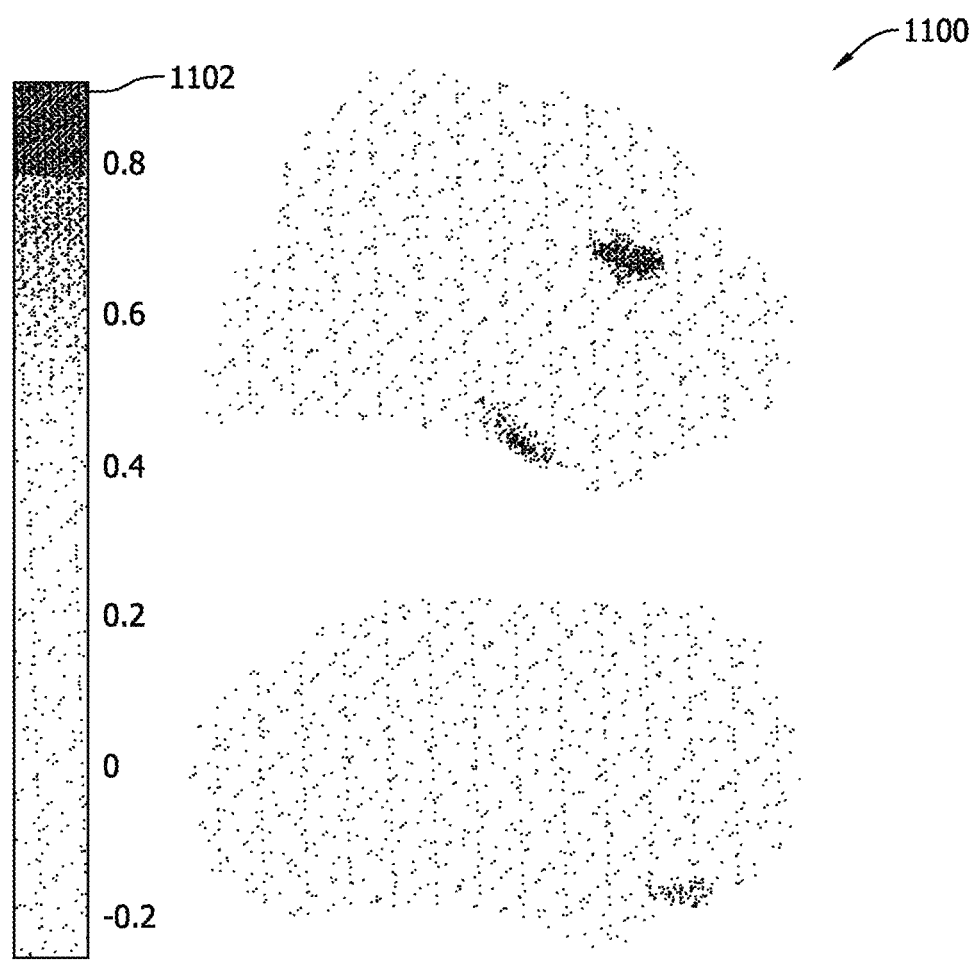
FIG. 11 is a diagram in which the scores from FIG. 10 have been transposed onto a three-dimensional geometry.

FIGS. 8-11 correspond to the example shown in FIGS. 4-7, and show the scores and transposition of scores onto the three-dimensional geometry for the second and third principal components. Specifically, FIG. 8 shows a graph 800 including scores for the second principal component. FIG. 9 shows a first diagram 902 with a first color scale 904 adjusted to emphasize scores in a first score window 802 of graph 800, and shows second diagrams 912 with a second color scale 914 adjusted to emphasize scores in a second score window 804 of graph 800. Similarly, FIG. 10 shows a graph 1000 including scores for the third principal component, and FIG. 11 shows a diagram 1100 with a color scale 1102 emphasizing scores in a score window 1002 of graph 1000.

FIGS. 12A-12C illustrate a comparison between existing ablation determination techniques and the systems and methods described herein. Specifically, FIG. 12A shows a three-dimensional geometry 1202 without any ablation information. FIG. 12B shows the same geometry 1202 post-procedurally, with actual ablation sites and fractionation locations identified. In this example, the ablation was performed by a clinician without using the systems and methods described herein.

FIG. 12C shows the same geometry 1202 including various regions of interest 1204 that are identified using PCA in accordance with the systems and methods described herein. Regions of interest 1204 include first regions of interest 1206 associated with the first principal component, second regions of interest 1208 associated with the second principal component, and third regions of interest 1210 associated with the third principal component. Further, fourth regions of interest 1212 are associated with more than one principal component (e.g., the first and second principal components). For illustration, the ablation sites and fractionation locations from FIG. 12B are overlaid onto geometry 1202 shown in FIG. 12C. As demonstrated by FIG. 12B, at least some of the potential ablation sites identified using the systems and methods described correspond to the actual ablation sites, but other potential ablation sites identified in FIG. 12C fall outside of the clinician-selected actual ablation sites of FIG. 12B. Accordingly, ablating per the identified potential ablation sites may generate improved results relative to the techniques used in FIG. 12B.

Figure 13E:
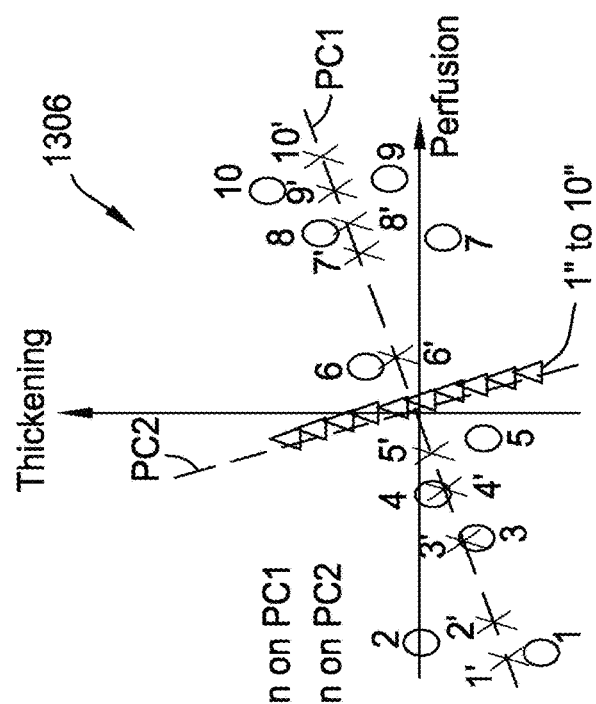
Figure 13D:
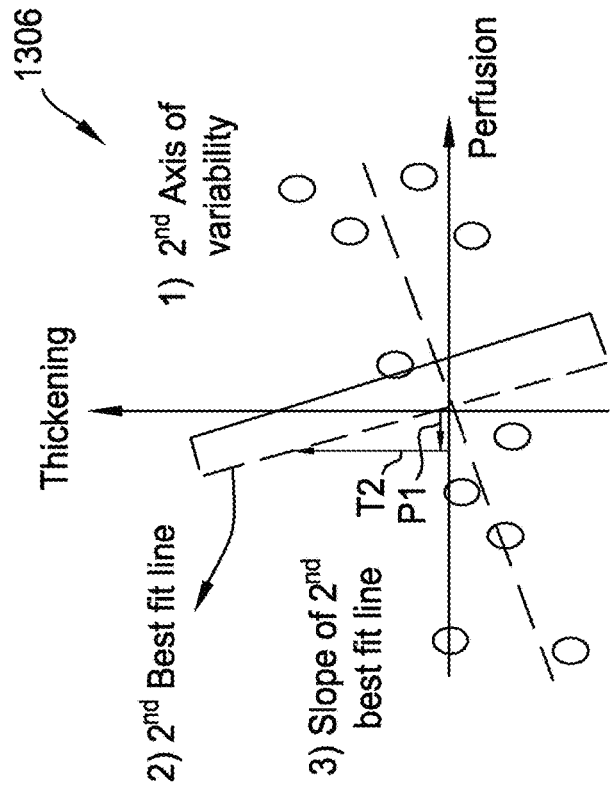

FIGS. 13A-13E illustrate steps for an example PCA analysis involving two parameters, tissue perfusion and thickening. FIG. 13A shows an initial dataset 1300 to be analyzed. In this example, initial dataset 1300 is a scatter plot of perfusion data versus thickening data. Then, as shown in graph 1302 of FIG. 13B, a first axis along which the data has the biggest dispersion is identified, a best fit line (i.e., the line minimizing a distance d between the line and each data point) is computed (also referred to as a first principal component (PC1)), and a slope of the best fit is determined. The best fit slope is determined based on loadings P1 and T1, with the loadings representing how each dataset variable contributes to the slope. In the diagrams shown, the x and y-axes are shifted (relative to the data points) between FIGS. 13A and 13B. This is because, to simplify the subsequent steps of the PCA analysis, a mean value of the original data set is subtracted from all values to center the dataset around the origin.

As shown in graph 1304 of FIG. 13C, the original data points are then projected onto the PC1 line to obtain a PC1 score for each data point (each score is illustrated as an 'X'). As shown in graph 1306 of FIG. 13D, this process is then repeated for an axis with the second biggest data dispersion (this second axis must be orthogonal to the first axis) to compute a second principal component (PC2) and determine a best fit slope based on loadings P2 and T2. Then, as shown in graph 1308 of FIG. 13E, the original data points are projected on to the PC2 line to obtain a PC2 score for each data point. When displayed on a 3D geometry, as described herein, pertinent scores enable displaying regions with high variability for each principal component.

Figure 14B:
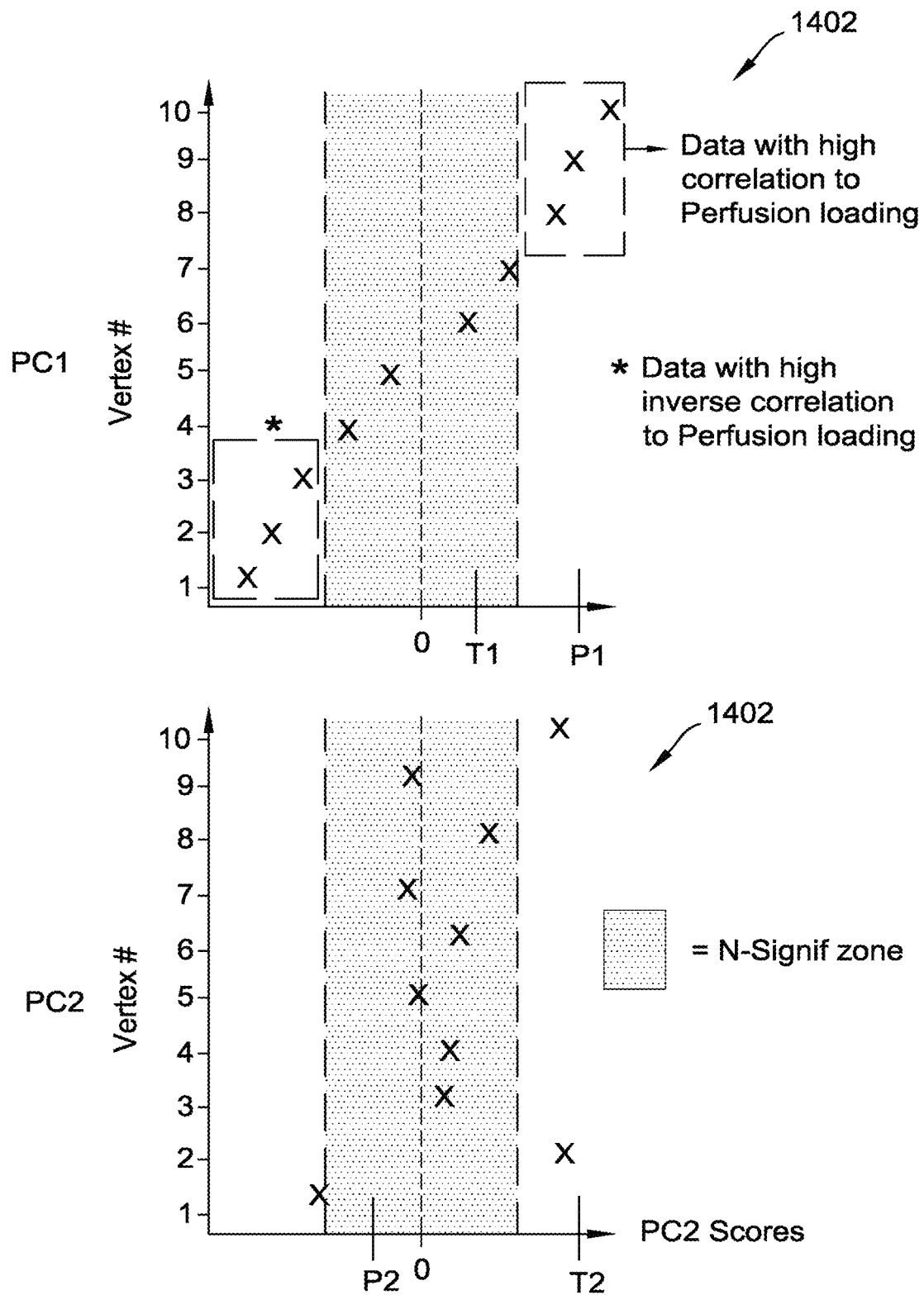
Figure 14D:
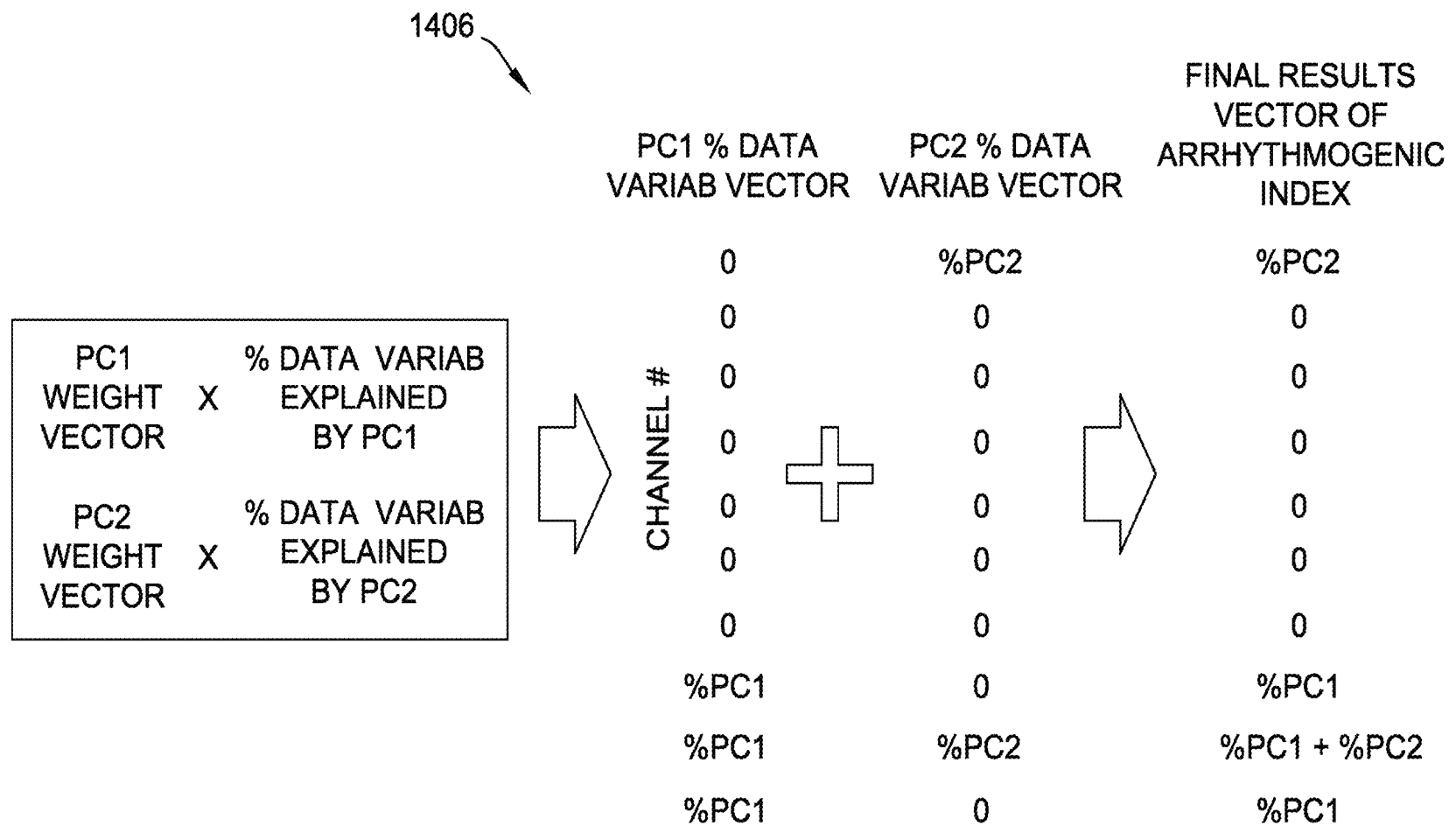
Figure 14E:
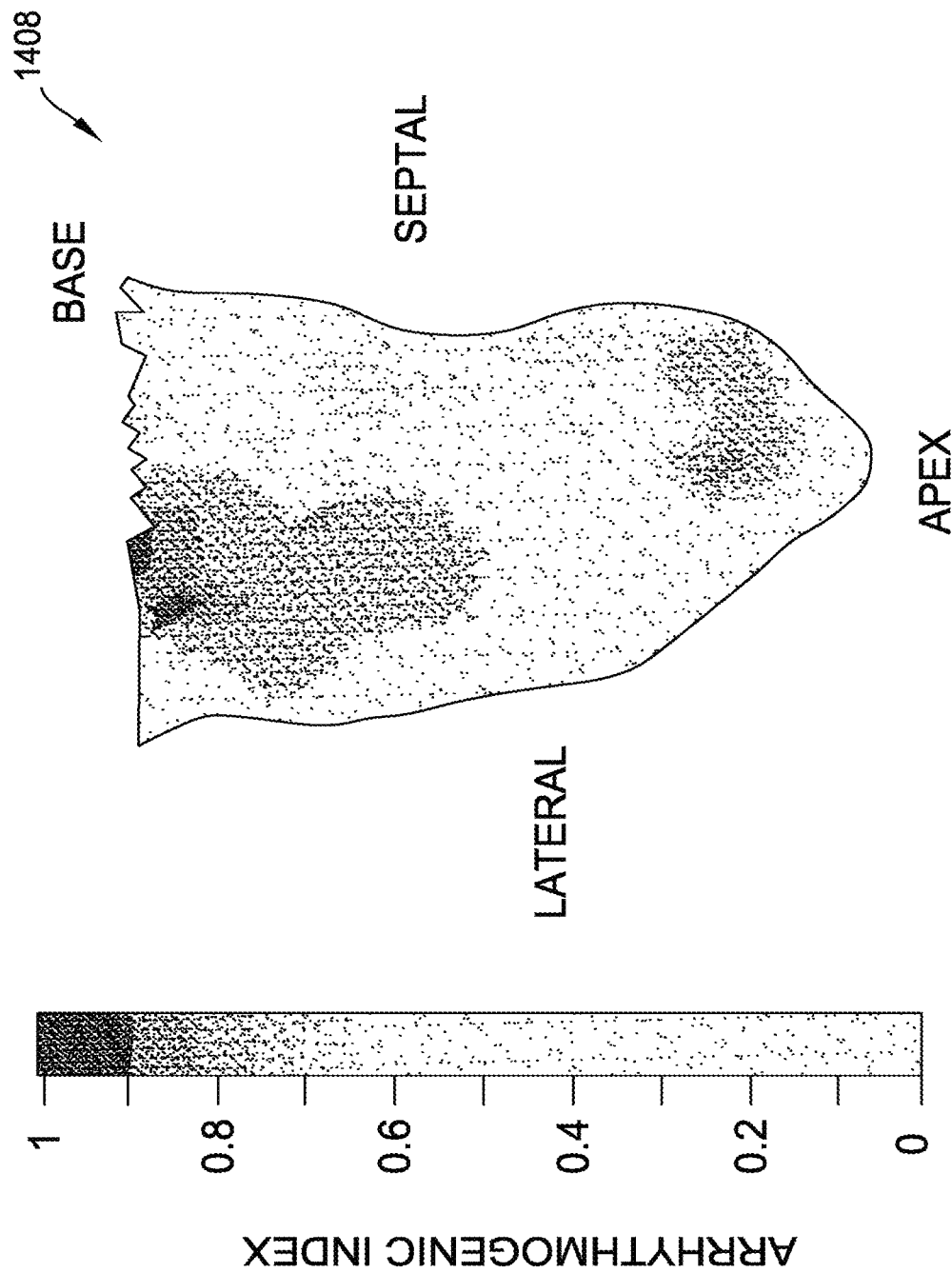

FIGS. 14A-14E illustrate steps for an example of PCA data processing performed to compute an arrhythmogenic index. The initial data is the same as that in the example of FIGS. 13A-13E. FIG. 14A shows graphs 1400 representing the data to be used for the processing (i.e., the principal component scores and loadings). As shown in graphs 1402 of FIG. 14B, the principal component scores are plotted on the x-axis, with their respective vertex number on the y-axis. Further, on each graph 1402, a threshold indicating which scores will be kept is also indicated. In addition, on each graph 1402, the loadings (P1, T1, P2, T2) are plotted on the x-axis.

The threshold is designed to keep scores that have the strongest correlation to the arrhythmogenic substrate. For example, the following steps may be taken to determine which scores to keep. First, scores with a high correlation to loadings corresponding to healthy tissue (e.g., scores representing LV areas with high perfusion, such as scores aligned with the P1 loading) are discarded. Then, for scores with a high correlation to pathologic tissue (e.g., scores representing LV areas with low perfusion, such as scores remote from the P1 loading), i) values between 70% to 100% of the highest value are kept, ii) if less than ten values are present in the 70% to 100% range, the lower limit is set to 50% instead of 70%, and iii) any scores with correlations less than 0.35 are discarded. Those of skill in the art will appreciate that this particular setting of the threshold is merely an example, and the threshold may be set using other suitable techniques.

FIG. 14C is a diagram 1404, illustrating applying a mask to the scores to generate a mask vector for each principal component. Specifically, scores that fall within the threshold are determined to be significant, and are set to 1, and scores that fall outside of the threshold are determined to be insignificant, and are set to 0 in this example. Subsequently, as shown in graph 1406 of FIG. 14D, the mask vector of each principal component is multiplied by the percentage of explained variance for that principal component, and the resulting vectors are summed to generate an arrhythmogenic index. The values of the arrhythmogenic index are then displayed on the corresponding vertices on the 3D geometry, as shown in graph 1408 of FIG. 14E.

The systems and methods described herein are directed to identifying potential ablation sites using principal component analysis (PCA). A method includes generating a dataset for analysis, the dataset including a plurality of variables and generated using imaging data associated with a three-dimensional geometry that includes a plurality of vertices. The method further includes performing PCA on the generated dataset to identify a plurality of principal components and to generate, for each vertex of the plurality of vertices, a score associated with each of the plurality of principal components. The method further includes transposing the scores for each vertex onto the three-dimensional geometry, and displaying the three-dimensional geometry including the transposed scores to facilitate identifying potential ablation sites.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A computer-implemented method for identifying potential ablation sites using principal component analysis (PCA), the method comprising:
   generating, using a computing device, a dataset for analysis, the dataset including a plurality of variables associated with a three-dimensional geometry that includes a plurality of vertices;
   performing, using the computing device, PCA on the generated dataset to identify a plurality of principal components and to generate, for each vertex of the plurality of vertices, a metric associated with each of the plurality of principal components; and
   transposing, using the computing device, the metrics for each vertex onto the three-dimensional geometry, wherein the transposed metrics facilitate identifying potential ablation sites.

2. The method of claim 1, wherein generating a dataset comprises generating a dataset including raw variables and processed variables.

3. The method of claim 2, further comprising calculating the processed variables for each vertex based on neighboring vertices located within a predetermined radius of the vertex.

4. The method of claim 1, further comprising normalizing the dataset prior to performing PCA.

5. The method of claim 1, wherein performing PCA comprises calculating a loading for each of the plurality of variables for each of the plurality of principal components.

6. The method of claim 1, further comprising displaying, using the computing device, the three-dimensional geometry including the transposed metrics.

7. The method of claim 1, wherein at least some of the plurality of variables are associated with perfusion.

8. A computing device for identifying potential ablation sites using principal component analysis (PCA), the computing device comprising:
   a memory device; and
   a processor communicatively coupled to the memory device, the processor configured to:
      generate a dataset for analysis, the dataset including a plurality of variables associated with a three-dimensional geometry that includes a plurality of vertices;
      perform PCA on the generated dataset to identify a plurality of principal components and to generate, for each vertex of the plurality of vertices, a metric associated with each of the plurality of principal components; and
      transpose the metrics for each vertex onto the three-dimensional geometry, wherein the transposed metrics facilitate identifying potential ablation sites.

9. The computing device of claim 8, wherein to generate a dataset, the processor is configured to generate a dataset including raw variables and processed variables.

10. The computing device of claim 9, wherein the processor is further configured to calculate the processed variables for each vertex based on neighboring vertices located within a predetermined radius of the vertex.

11. The computing device of claim 8, wherein the processor is further configured to normalize the dataset prior to performing PCA.

12. The computing device of claim 8, wherein to perform PCA, the processor is configured to calculate a loading for each of the plurality of variables for each of the plurality of principal components.

13. The computing device of claim 8, wherein the processor is further configured to display the three-dimensional geometry including the transposed metrics.

14. The computing device of claim 8, wherein at least some of the plurality of variables are associated with perfusion.

15. Non-transitory computer-readable media having computer-executable instructions thereon, wherein when executed by a processor of a computing device, cause the processor of the computing device to:
generate a dataset for analysis, the dataset including a plurality of variables and associated with a three-dimensional geometry that includes a plurality of vertices;
perform PCA on the generated dataset to identify a plurality of principal components and to generate, for each vertex of the plurality of vertices, a metric associated with each of the plurality of principal components; and
transpose the metrics for each vertex onto the three-dimensional geometry, wherein the transposed metrics facilitate identifying potential ablation sites.

16. The non-transitory computer-readable media of claim 15, wherein to generate a dataset, the processor is configured to generate a dataset including raw variables and processed variables.

17. The non-transitory computer-readable media of claim 16, wherein the computer-executable instructions are configured to further cause the processor to calculate the processed variables for each vertex based on neighboring vertices located within a predetermined radius of the vertex.

18. The non-transitory computer-readable media of claim 15, wherein the computer-executable instructions are configured to further cause the processor to normalize the dataset prior to performing PCA.

19. The non-transitory computer-readable media of claim 15, wherein to perform PCA, the computer-executable instructions are configured to cause the processor to calculate a loading for each of the plurality of variables for each of the plurality of principal components.

20. The non-transitory computer-readable media of claim 15, wherein the computer-executable instructions are configured to further cause the processor to display the three-dimensional geometry including the transposed metrics.

* * * * *